US011534223B2

(12) United States Patent
Ortiz et al.

(10) Patent No.: US 11,534,223 B2
(45) Date of Patent: Dec. 27, 2022

(54) PEDICLE SCREW REMOVAL TOOL AND METHOD OF USE

(71) Applicant: Orthopedic Renovation Technologies, LLC, San Antonio, TX (US)

(72) Inventors: Rene Ortiz, Helotes, TX (US); Alejandro Rene Ortiz, Helotes, TX (US)

(73) Assignee: Orthopedic Renovation Technologies, LLC, San Antonio, TX (US)

( * ) Notice: Subject to any disclaimer, the term of this patent is extended or adjusted under 35 U.S.C. 154(b) by 100 days.

(21) Appl. No.: 16/949,562

(22) Filed: Nov. 3, 2020

(65) Prior Publication Data

US 2021/0068882 A1 Mar. 11, 2021

Related U.S. Application Data

(63) Continuation-in-part of application No. 15/344,152, filed on Nov. 4, 2016, now Pat. No. 10,820,936.

(51) Int. Cl.
*A61F 2/44* (2006.01)
*A61F 2/46* (2006.01)
(Continued)

(52) U.S. Cl.
CPC .......... *A61B 17/92* (2013.01); *A61B 17/8875* (2013.01)

(58) Field of Classification Search
CPC ............ A61B 17/8875; A61B 17/8877; A61B 17/8615; A61B 17/861; A61B 17/7079;
(Continued)

(56) References Cited

U.S. PATENT DOCUMENTS 1,741,810 A * 12/1929 Bidal ................... B25G 1/005
  81/177.2
1,775,402 A * 9/1930 Mandl ................... B25B 13/56
  81/177.75
(Continued)

FOREIGN PATENT DOCUMENTS

CN 203226891 10/2013
CN 204446088 7/2015
(Continued)

OTHER PUBLICATIONS

CN 203226891 machine translation, Aug. 24, 2017.
CN 204446088 machine translation, Aug. 24, 2017.

*Primary Examiner* — Jessica Weiss
(74) *Attorney, Agent, or Firm* — Schultz & Associates, P.C.

(57) ABSTRACT

Disclosed is a universal pedicle screw removal tool comprising a tapered shaft having an "L" shaped tip on one end and a generally square head on an opposite end. A lower section leads to a tapered section which is connected to a handle. The handle may include a set of serrations to provide increased grip. The handle is connected to the head. The tip is sized to engage the channel of a tuliped pedicle screw while the head is sized to engage a ratchet or other torque producing tool. In an alternate embodiment, the tip is "T" shaped. In another alternate embodiment, the handle section includes opposing members extending from the shaft to form a "T" shaped handle. In use, the tip is inserted into the channel of a tuliped pedicle screw while the shaft is rotated to unscrew the pedicle screw from a patient's bone.

21 Claims, 10 Drawing Sheets

(51) Int. Cl.
*A61B 17/92* (2006.01)
*A61B 17/88* (2006.01)

(58) Field of Classification Search
CPC ............ A61B 17/7076; A61B 17/7032; A61B 17/7082; B25B 13/481; B25B 23/0021; B25B 23/0035; B25G 1/04; B25G 1/005; A61C 8/009; A61C 8/0092; A61C 8/0089; A61C 8/0096
USPC ............ 606/70–71, 280–299, 201, 217, 226, 606/235–243, 104; 81/177.2; 132/73.5–76.5; 433/124, 143
See application file for complete search history.

(56) References Cited

U.S. PATENT DOCUMENTS

| | | | | |
|---|---|---|---|---|
| 1,835,315 | A * | 12/1931 | Mclay | B25G 1/007 81/177.9 |
| 2,530,914 | A * | 11/1950 | Simmons | B25B 13/5091 81/52 |
| 2,697,370 | A * | 12/1954 | Linzyw | B25B 13/466 81/58 |
| 2,814,322 | A * | 11/1957 | Kupfrian | B25B 13/481 81/64 |
| 3,882,753 | A * | 5/1975 | Svensen | B25B 13/06 81/177.7 |
| 3,935,640 | A * | 2/1976 | Cohan | A61C 3/00 433/150 |
| 3,972,252 | A * | 8/1976 | Hunter | B25B 13/467 81/57.29 |
| 4,334,445 | A * | 6/1982 | Timewell | B25G 1/063 81/177.7 |
| 5,148,724 | A * | 9/1992 | Rexford | B25B 13/06 81/124.4 |
| 5,184,724 | A | 2/1993 | Mayled | |
| D334,516 | S * | 4/1993 | Tsunoda | D8/29 |
| 5,536,268 | A | 7/1996 | Griss | |
| D393,318 | S | 4/1998 | Wolter | |
| D402,757 | S | 12/1998 | Davis et al. | |
| 5,899,901 | A * | 5/1999 | Middleton | A61B 17/7032 606/102 |
| 5,950,507 | A * | 9/1999 | Wolfe | B25B 21/007 81/177.2 |
| D418,601 | S | 1/2000 | McGugan | |
| 6,089,128 | A * | 7/2000 | Kopyless | B25B 13/48 81/124.7 |
| D445,899 | S | 7/2001 | McLeod et al. | |
| 6,286,396 | B1 * | 9/2001 | Johnson | B25B 9/00 81/177.2 |
| 6,427,564 | B1 * | 8/2002 | Nelson | B25G 1/005 81/177.1 |
| D483,475 | S | 12/2003 | Kirwan et al. | |
| D490,152 | S | 5/2004 | Myall et al. | |
| D492,995 | S | 7/2004 | Rue et al. | |
| D496,730 | S | 9/2004 | Morawski et al. | |
| D515,214 | S | 2/2006 | Jackson, III et al. | |
| D516,895 | S | 3/2006 | Minkler et al. | |
| D530,680 | S | 10/2006 | Fox et al. | |
| D531,310 | S | 10/2006 | Wolter et al. | |
| D551,994 | S | 10/2007 | Ahsen-Bore | |
| D565,733 | S | 4/2008 | Andre | |
| D571,010 | S | 6/2008 | Cote | |
| D581,530 | S | 11/2008 | Thierfelder et al. | |
| 7,470,279 | B2 | 12/2008 | Jackson | |
| D590,946 | S | 4/2009 | Baynham | |
| 7,677,140 | B2 * | 3/2010 | Hull | B25B 13/461 16/429 |
| D616,095 | S | 5/2010 | Kim et al. | |
| D619,243 | S | 7/2010 | Petersen et al. | |
| D622,843 | S | 8/2010 | Horton | |
| D627,460 | S | 11/2010 | Horton | |
| D629,896 | S | 12/2010 | Horton | |
| D634,843 | S | 3/2011 | Kim et al. | |
| D636,873 | S | 4/2011 | Palmer et al. | |
| D642,268 | S | 7/2011 | Qureshi | |
| 8,065,938 | B1 * | 11/2011 | Kravitch | B25B 13/48 81/177.2 |
| 8,117,951 | B2 * | 2/2012 | Brobst | B25G 3/38 81/177.2 |
| D655,414 | S | 3/2012 | Cuschieri et al. | |
| 8,202,303 | B2 | 6/2012 | Zehnder | |
| D669,983 | S | 10/2012 | Dapri et al. | |
| D670,381 | S | 11/2012 | Dapri et al. | |
| D679,014 | S | 3/2013 | Jayaraj | |
| D680,396 | S * | 4/2013 | He | D8/21 |
| 8,414,628 | B2 | 4/2013 | Melkent | |
| D685,092 | S | 6/2013 | Morawski et al. | |
| 8,469,960 | B2 | 6/2013 | Hutton et al. | |
| D691,274 | S | 10/2013 | Buckets et al. | |
| D693,470 | S | 11/2013 | Fagan | |
| D694,891 | S | 12/2013 | Dietrich | |
| 8,617,210 | B2 | 12/2013 | Sicvol et al. | |
| D703,707 | S | 4/2014 | Foster et al. | |
| 8,709,015 | B2 * | 4/2014 | Kolb | A61B 17/7032 606/246 |
| D704,836 | S | 5/2014 | Shiao | |
| D708,324 | S | 7/2014 | Schwarz et al. | |
| D708,754 | S | 7/2014 | Harangvolgyi | |
| 8,845,649 | B2 | 9/2014 | Jackson | |
| 8,852,239 | B2 | 10/2014 | Jackson et al. | |
| D719,651 | S | 12/2014 | Hoffmann et al. | |
| D724,725 | S | 3/2015 | Chang | |
| 8,986,349 | B1 | 3/2015 | German et al. | |
| 9,033,988 | B2 * | 5/2015 | Gephart | A61B 17/3421 606/86 A |
| D735,327 | S | 7/2015 | Van Wyk et al. | |
| D736,917 | S | 8/2015 | Katsura | |
| D736,923 | S | 8/2015 | Snow | |
| D737,440 | S | 8/2015 | Shabaz | |
| 9,101,416 | B2 | 8/2015 | Dunbar, Jr. et al. | |
| 9,125,694 | B2 | 9/2015 | Butler et al. | |
| D740,422 | S | 10/2015 | Herfort | |
| D741,483 | S | 10/2015 | Solingen et al. | |
| 9,198,698 | B1 | 12/2015 | Doose et al. | |
| D747,802 | S | 1/2016 | Freigang et al. | |
| D748,254 | S | 1/2016 | Freigang et al. | |
| 9,241,738 | B2 | 1/2016 | Quevedo et al. | |
| 9,289,249 | B2 | 3/2016 | Ramsey | |
| 9,295,500 | B2 | 3/2016 | Marigowda | |
| 9,295,501 | B2 | 3/2016 | Hammer | |
| 9,320,550 | B2 | 4/2016 | Hutton et al. | |
| D755,368 | S | 5/2016 | Efinger et al. | |
| D755,383 | S | 5/2016 | Pfister et al. | |
| 9,326,798 | B2 | 5/2016 | Kolb et al. | |
| D758,565 | S | 6/2016 | Efinger et al. | |
| 9,370,384 | B2 | 6/2016 | Mitchell et al. | |
| 9,409,286 | B2 | 8/2016 | Hsu | |
| D765,841 | S | 9/2016 | Schuerg | |
| D765,842 | S | 9/2016 | Schuerg | |
| D766,432 | S | 9/2016 | Schuerg | |
| D767,760 | S | 9/2016 | Suwito et al. | |
| D770,044 | S | 10/2016 | Fiksen et al. | |
| D770,618 | S | 11/2016 | Fiksen et al. | |
| D772,412 | S | 11/2016 | Efinger et al. | |
| D776,259 | S | 1/2017 | Eldredge | |
| D776,260 | S | 1/2017 | Eldredge | |
| D779,053 | S | 2/2017 | Kobida et al. | |
| D785,796 | S | 5/2017 | Efinger et al. | |
| D786,429 | S | 5/2017 | Cummins et al. | |
| D787,675 | S | 5/2017 | Salehi | |
| D791,318 | S | 7/2017 | Jutila et al. | |
| D794,192 | S | 8/2017 | Schuerg | |
| D794,193 | S | 8/2017 | Schuerg | |
| D794,194 | S | 8/2017 | Schuerg | |
| D795,424 | S | 8/2017 | Sloss | |
| D799,040 | S | 10/2017 | Melnikoff et al. | |
| D799,043 | S | 10/2017 | Storch | |
| 9,814,497 | B1 | 11/2017 | Al-Habib et al. | |
| D807,139 | S | 1/2018 | Riskin et al. | |
| D833,607 | S | 11/2018 | Aradono et al. | |
| D833,614 | S | 11/2018 | Lange et al. | |
| D834,702 | S | 11/2018 | Evans et al. | |

(56) References Cited

U.S. PATENT DOCUMENTS

| | | |
|---|---|---|
| D840,031 S | 2/2019 | Teufel |
| D846,738 S | 4/2019 | Kalina, Jr. et al. |
| D847,988 S | 5/2019 | Schnitzer |
| D851,273 S | 6/2019 | Frezal |
| D853,561 S | 7/2019 | Guo |
| 10,349,985 B1 | 7/2019 | Kriete et al. |
| D866,766 S | 11/2019 | Cahill |
| D870,897 S | 12/2019 | Katzberg |
| 10,524,805 B2 | 1/2020 | Zilberman et al. |
| D877,328 S | 3/2020 | Alsiddiky et al. |
| D879,960 S | 3/2020 | Melnikoff et al. |
| D879,965 S | 3/2020 | Su et al. |
| D882,084 S | 4/2020 | Qun |
| D882,788 S | 4/2020 | Qun |
| D882,790 S | 4/2020 | Qun |
| D884,889 S | 5/2020 | Cahill |
| 10,709,231 B2 | 7/2020 | Macomber |
| D895,107 S | 9/2020 | Zhang |
| D896,368 S | 9/2020 | Zhang |
| D897,815 S | 10/2020 | Hsieh |
| D898,914 S | 10/2020 | Niver et al. |
| D901,683 S | 11/2020 | Kalina et al. |
| D903,100 S | 11/2020 | Stats et al. |
| 10,820,936 B2 | 11/2020 | Ortiz et al. |
| D910,836 S | 2/2021 | Sandberg et al. |
| D911,521 S | 2/2021 | Swift et al. |
| D918,382 S | 5/2021 | Naughton et al. |
| 2002/0169453 A1 | 11/2002 | Berger |
| 2003/0216743 A1* | 11/2003 | Hoffman .............. A61B 17/0401 606/99 |
| 2003/0217623 A1* | 11/2003 | Brown .................... B25B 13/48 81/437 |
| 2005/0140062 A1* | 6/2005 | Shimomura .............. B22C 7/06 264/334 |
| 2005/0149052 A1* | 7/2005 | Meek .................... A61F 2/4637 606/104 |
| 2005/0228400 A1 | 10/2005 | Chao et al. |
| 2005/0273167 A1* | 12/2005 | Triplett .............. A61B 17/1671 623/17.11 |
| 2008/0076089 A1* | 3/2008 | Vu ........................... A61C 3/00 433/143 |
| 2008/0082103 A1 | 4/2008 | Hutton et al. |
| 2008/0154280 A1* | 6/2008 | Schumacher ...... A61B 17/7083 606/104 |
| 2008/0221583 A1 | 9/2008 | Sharifi-Mehr et al. |
| 2009/0187194 A1* | 7/2009 | Hamada ............. A61B 17/7001 606/104 |
| 2009/0217789 A1* | 9/2009 | Chang .................. B25B 13/465 81/60 |
| 2009/0248088 A1 | 10/2009 | Biedermann |
| 2010/0087823 A1 | 4/2010 | Kondrashov |
| 2012/0046665 A1 | 2/2012 | Kim |
| 2012/0123516 A1 | 5/2012 | Gerdts et al. |
| 2013/0090698 A1* | 4/2013 | Nuckley ............. A61B 17/7082 606/308 |
| 2013/0331892 A1 | 12/2013 | Peterson et al. |
| 2014/0026724 A1* | 1/2014 | Broadaway ............... B25G 1/00 81/489 |
| 2014/0288567 A1* | 9/2014 | Kroll .................. A61B 17/8886 606/104 |
| 2015/0066042 A1* | 3/2015 | Cummins .......... A61B 17/7037 606/104 |
| 2015/0335452 A1 | 11/2015 | Rao et al. |
| 2016/0074075 A1 | 3/2016 | Beyar et al. |
| 2017/0027612 A1 | 2/2017 | Viart et al. |
| 2017/0129078 A1* | 5/2017 | Gatling ............... B25B 13/5091 |
| 2018/0125559 A1 | 5/2018 | Ortiz et al. |
| 2018/0146990 A1 | 5/2018 | Manzanares et al. |
| 2019/0083147 A1 | 3/2019 | Hackathorn, II |
| 2019/0142471 A1 | 5/2019 | Lindner |
| 2020/0093522 A1 | 3/2020 | Zink et al. |
| 2021/0052403 A1 | 2/2021 | Chu et al. |
| 2021/0068882 A1 | 3/2021 | Ortiz et al. |

FOREIGN PATENT DOCUMENTS

| | | |
|---|---|---|
| DE | 4238339 C2 | 5/1994 |
| DE | 10005386 A1 | 8/2001 |
| EP | 0571619 B1 | 12/1993 |
| FR | 2650173 A1 | 2/1991 |
| FR | 2659546 A1 | 9/1991 |
| FR | 2778089 A1 | 11/1999 |
| WO | 9410944 A1 | 5/1994 |
| WO | 9514437 A1 | 6/1995 |
| WO | 2011133160 A1 | 10/2011 |
| WO | 2012057386 A1 | 5/2012 |
| WO | 2014142797 A1 | 9/2014 |
| WO | 2014204076 A1 | 12/2014 |

* cited by examiner

PEDICLE SCREW REMOVAL TOOL AND METHOD OF USE

CROSS-REFERENCE TO RELATED APPLICATIONS

This application is a continuation-in-part of application Ser. No. 15/344,152, filed on Nov. 4, 2016, now U.S. Pat. No. 10,820,936. Each patent application identified above is incorporated here by reference in its entirety to provide continuity of disclosure.

FIELD OF THE INVENTION

The present disclosure relates to tools for use during spinal surgery. In particular, the present disclosure relates to a pedicle screw removal tool.

BACKGROUND OF THE INVENTION

Spinal fusion, also called spondylodesis or spondylosyndesis, is a neurosurgical surgical technique that joins two or more vertebrae. Supplementary bone tissue or artificial bone is used to augment natural bone growth processes to fuse two or more adjoining vertebrae. When additional stability is required, vertebrae can be stabilized with screws through the pedicles of each vertebrae and connected with a stability rod.

Figure 1:
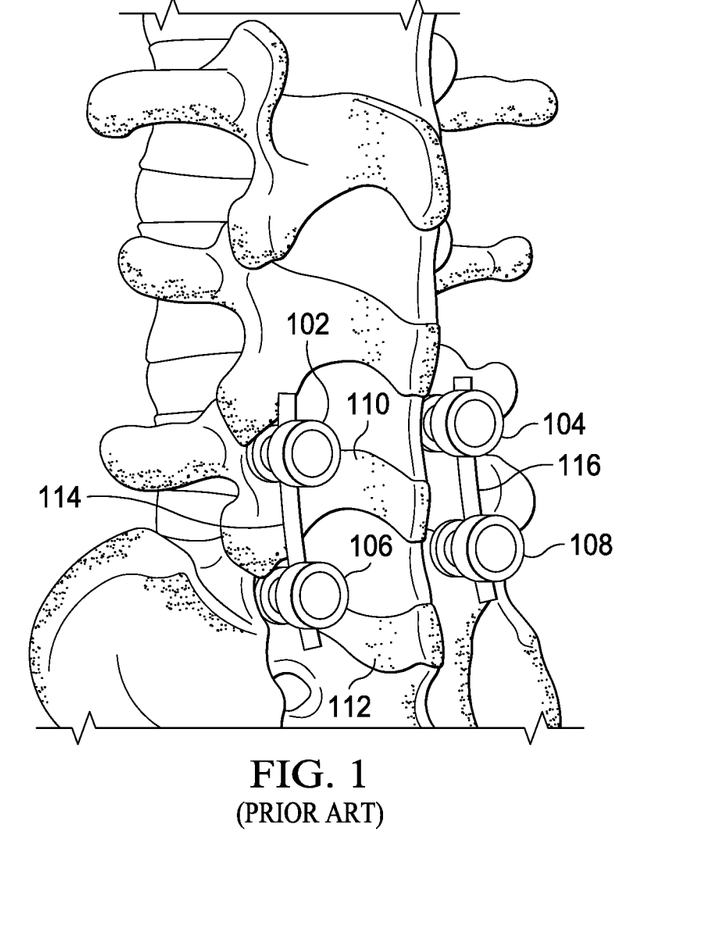
FIG. 1 is an isometric view of vertebrae anchored by pedicle screws and stability rods as known in the prior art.

FIG. 1 shows four pedicle screws 102, 104, 106, and 108 anchored in the pedicles of two adjoining vertebrae 110 and 112. Stability rod 114 is anchored by pedicle screws 102 and 106. Stability rod 116 is anchored by pedicle screws 104 and 108.

A pedicle screw is a particular type of bone screw designed for implantation during a spinal fusion procedure. A common type of pedicle screw is a "tuliped" pedicle screw that is comprised of a "U" shaped body affixed to a threaded section. The "U" shaped body presents a channel for seating the rod. A threaded end cap engages the body to secure the rod to the screw. The body includes a machined recess shaped for receiving a screwdriver type tool which is used to implant and remove the pedicle screw.

Figure 2A:
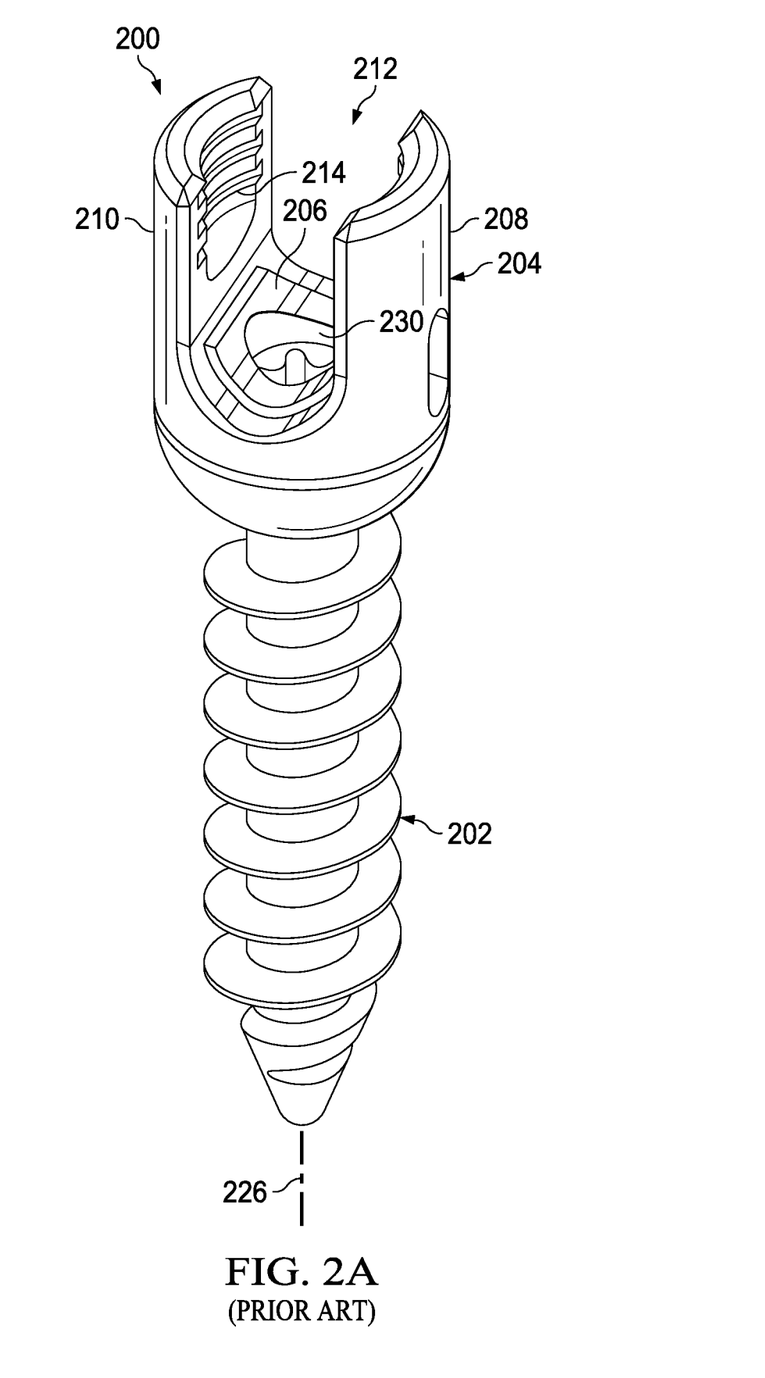
FIG. 2A is an isometric view of a tuliped pedicle screw as known in the prior art.
Figure 2B:
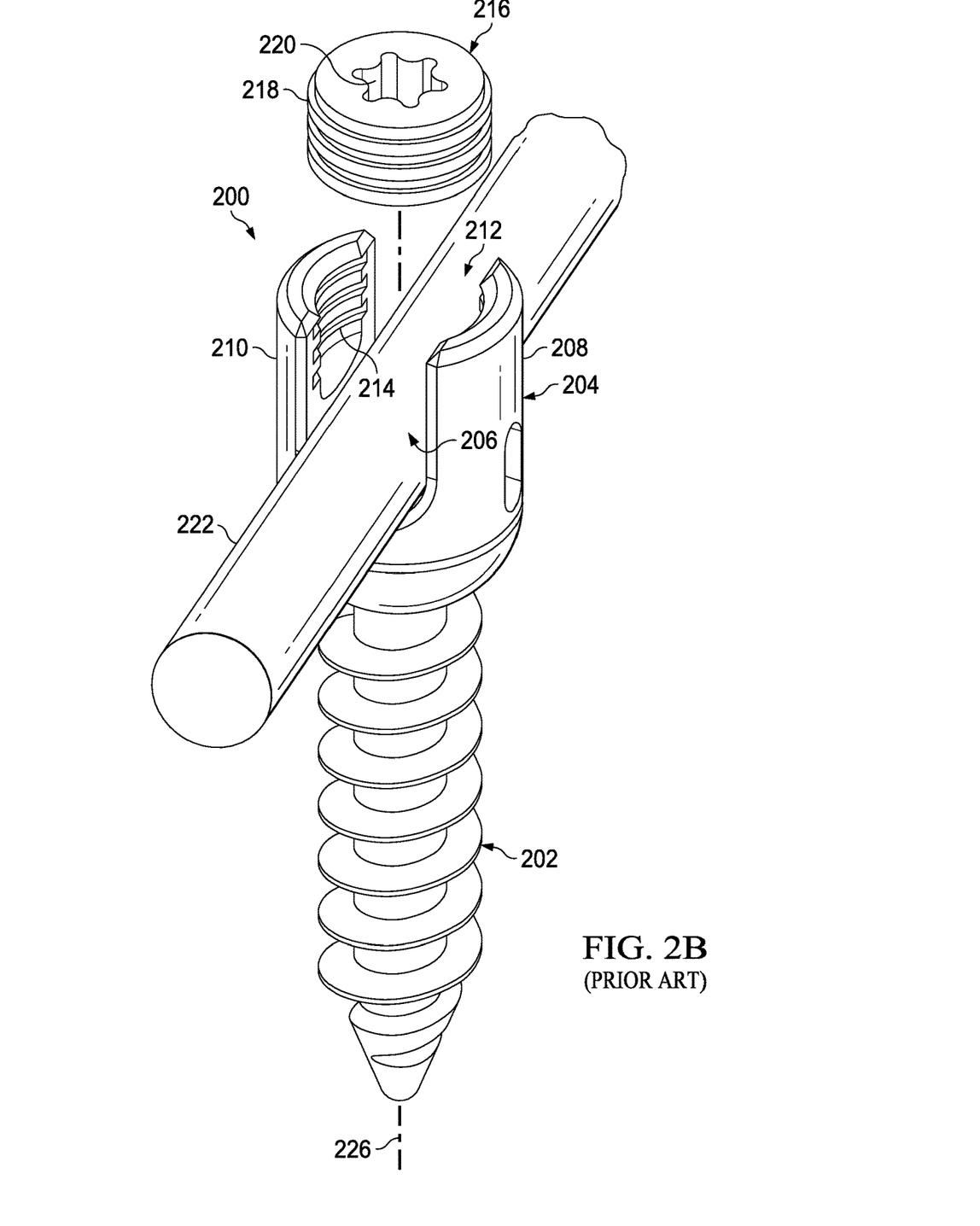
FIG. 2B is an exploded isometric view of a tuliped pedicle screw engaged with a stability rod as known in the prior art.

Referring to FIGS. 2A and 2B, the components of a common tuliped pedicle screw are shown. Pedicle screw 200 comprises threaded section 202 connected to body 204. Threaded section 202 has longitudinal axis 226. Body 204 forms channel 206 between blades 208 and 210. Body 204 includes opening 212 opposite threaded section 202. Opening 212 leads to channel 206. At the base of the channel, the tuliped pedicle screw includes socket 230 used to install the screw into bone. Internal thread 214 is formed on each blade 208 and 210 proximate opening 212. End cap 216 is disc shaped and includes exterior thread 218 sized to engage internal thread 214. End cap 216 further defines socket 220 shaped to receive a screwdriver type tool. Rod 222 fits within in channel 206. End cap 216 is threadably engaged with body 204 and secures rod 222 to pedicle screw 200.

Occasionally it is necessary to remove the pedicle screws after successful spinal fusion and stability are achieved. During surgery, a universal removal tray is utilized. The tray is equipped with many tools necessary to accommodate the different sizes and shapes of pedicle screws. Removal can be difficult because often the screws have become incarcerated in the bone and will not turn easily. Further, the body socket is many times filled with boney growth. The boney growth makes insertion of a removal tool difficult. As a result, the channel and the body socket is often stripped, bent, or broken during the removal procedure.

Several techniques have been developed to effect removal of a pedicle screw once its integrity is compromised. For example, one technique involves bisecting the stability rod, and securing it to the screw with an end cap. Pliers are then used to hold the rod and apply torque to the screw. This method creates a problem because ends of the rod can cause damage to the surrounding tissue leading to substantial bleeding and prolonged recovery time. As a second example, a cutting wheel may be used to notch the top of the screw in order to facilitate the use of a bladed removal tool. A problem with this approach is that metal shavings resulting from the procedure resist removal through irrigation and can contaminate the surrounding tissue. A more serious problem is that the cutting wheel, if not used carefully, may damage the spinal cord causing paralysis.

Hence, there is a need for a pedicle screw removal device that can be universally used for all sizes and shapes of tuliped pedicle screws that will function to cleanly remove a compromised screw without risk of contamination or damage to surrounding tissues.

SUMMARY OF THE INVENTION

A preferred embodiment is comprised of a tapered shaft having a right angle removal tip formed as its distal end and a generally square head on the proximal end. The removal tip is integrally formed with a tapered section which expands the overall circumference of the shaft. The tapered section leads to a cylindrically shaped handle section. The handle section may include a set of serrations. The removal tip is sized to match a stability rod and to easily engage the channel of a tuliped pedicle screw. The square head is designed to accommodate a ratchet or "T" handle.

In an alternate embodiment, the removal tip includes opposing prongs.

In another alternate embodiment, the handle section includes opposing members extending from the shaft to form a "T" shaped handle. Any combination of the alternate embodiments of the tip and handle is envisioned.

In use, the removal tip is inserted into the channel of a tuliped pedicle screw and secured to the screw with an end cap. The shaft is rotated via the handle section or with a torque producing tool attached to the head. The shaft is rotated along its longitudinal axis in a rotational direction that unscrews the pedicle screw from the bone. The removal tip eliminates the need for removal of boney tissue from the body socket or, alternatively, is useful after the body socket is compromised during removal.

Those skilled in the art will appreciate the above-mentioned features and advantages of the disclosure together with other important aspects upon reading the detailed description that follows in conjunction with the drawings.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness.

Figure 3A:
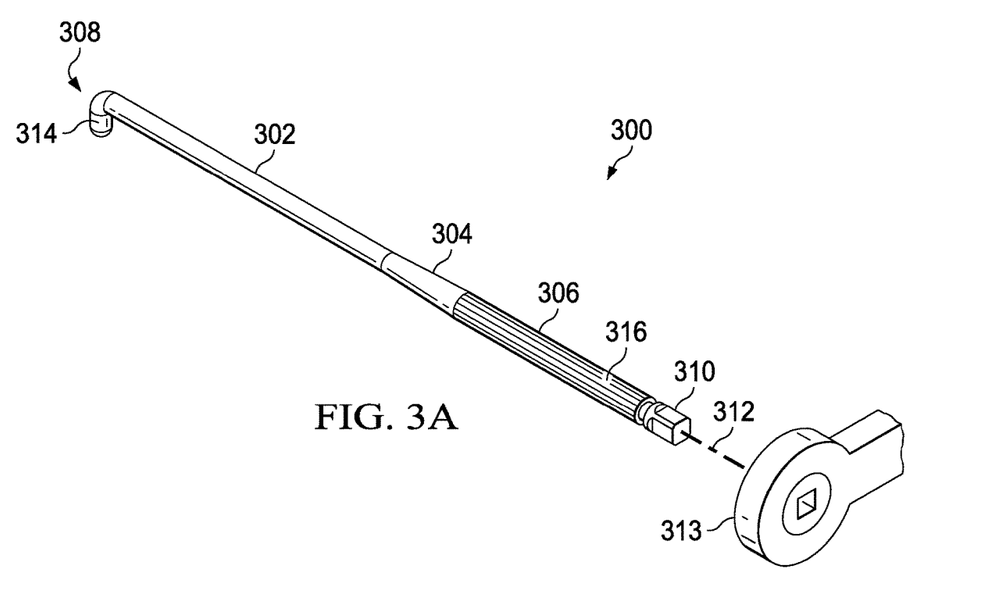
FIG. 3A is an isometric view of a preferred embodiment.
Figure 3B:
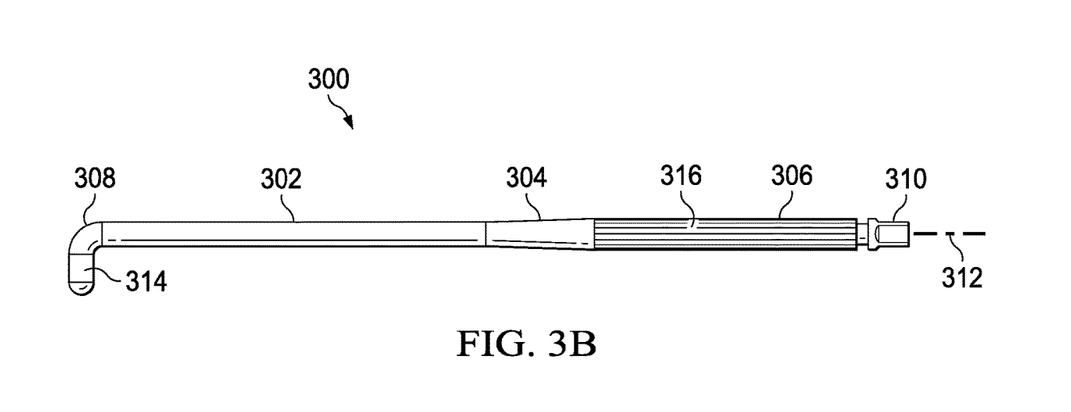
FIG. 3B is a side view of the preferred embodiment of FIG. 3A.

Referring to FIGS. 3A and 3B, pedicle screw removal tool 300 is a generally tapered cylindrical shaft comprising lower section 302 integrally formed with neck 304. Neck 304 is integrally formed with handle 306. Tip 308 is integrally formed with lower section 302 opposite neck 304. Head 310 is integrally formed with handle 306 opposite neck 304. Torque imposing tool 313 is removably attached to the head. The torque imposing tool may be, for example, a ratchet adaptor which applies torque in only one rotational direction. In another example, the torque imposing tool can be a simple crescent wrench. In yet another example, the torque imposing tool can be a torque wrench indicating the amount of torque applied to prevent shearing of the pedicle screw shaft. Lower section 302 is axially aligned with neck 304. Neck 304 is axially aligned with handle 306. Handle 306 is axially aligned with head 310. Lower section 302, neck 304, handle 306, and head 310 all share central longitudinal axis 312. Tip 308 is generally "L" shaped formed by prong 314. Prong 314 extends from tip 308 generally perpendicular to lower section 302. In a preferred embodiment, pedicle screw removal tool 300 is constructed of surgical grade stainless steel.

The overall length of pedicle screw removal tool 300 can range from approximately eight to twelve inches depending on desired use. Prong 314 generally ranges from ⅛ to ½ inch in diameter. All dimensions are provided with a ±5% tolerance. The length of prong 314 ranges from approximately ½ to one inch. Lower section 302 ranges in length from approximately three to five inches. Lower section 302 generally ranges from ⅛ to ½ inch in diameter. The length of neck 304 ranges from approximately one to two inches. Neck 304 is a generally frustoconical shape with an increasing diameter from a range of ⅛ to ½ inch in diameter at the connection of neck 304 to lower section 302 to a range of ½ inch to ¾ inch in diameter at the connection of neck 304 to handle 306. Handle 306 ranges in length from approximately three to four inches. Handle 306 generally ranges from ½ to ¾ inch in diameter. In an alternate embodiment, handle 306 may include serrations 316. Head 310 ranges in length from approximately ½ to one inch. Head 310 has a generally square cross-section width a width that ranges from approximately ⅛ to ¾ of an inch. In alternate embodiments, head 310 may have other polygonal cross-sectional shapes suitable for attachment of the torque imposing tool.

Figure 4A:
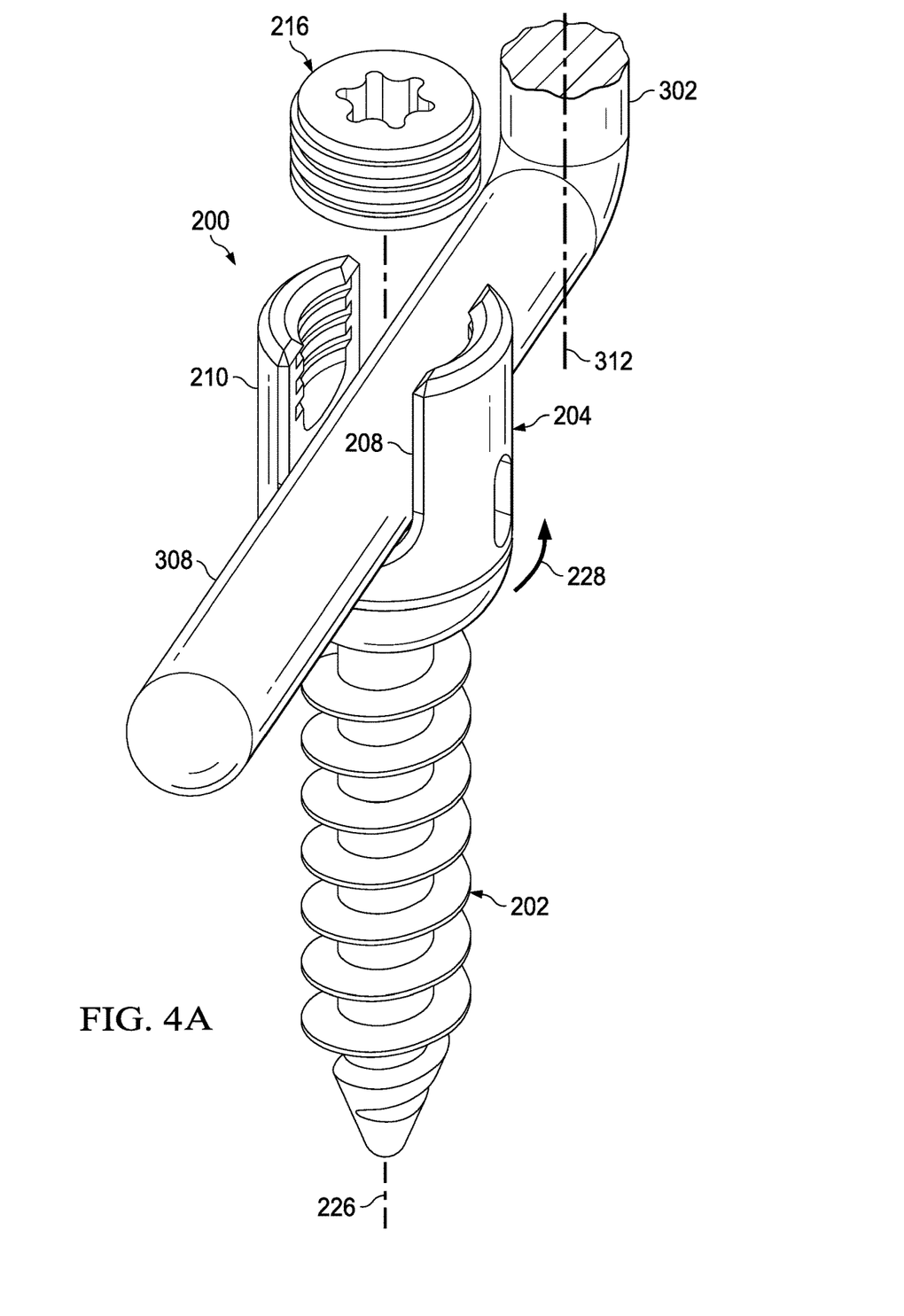
FIG. 4A is an isometric view of the preferred embodiment of FIG. 3A positioned so that the longitudinal axis of the screw is coplanar with the longitudinal axis of the tool.
Figure 4B:
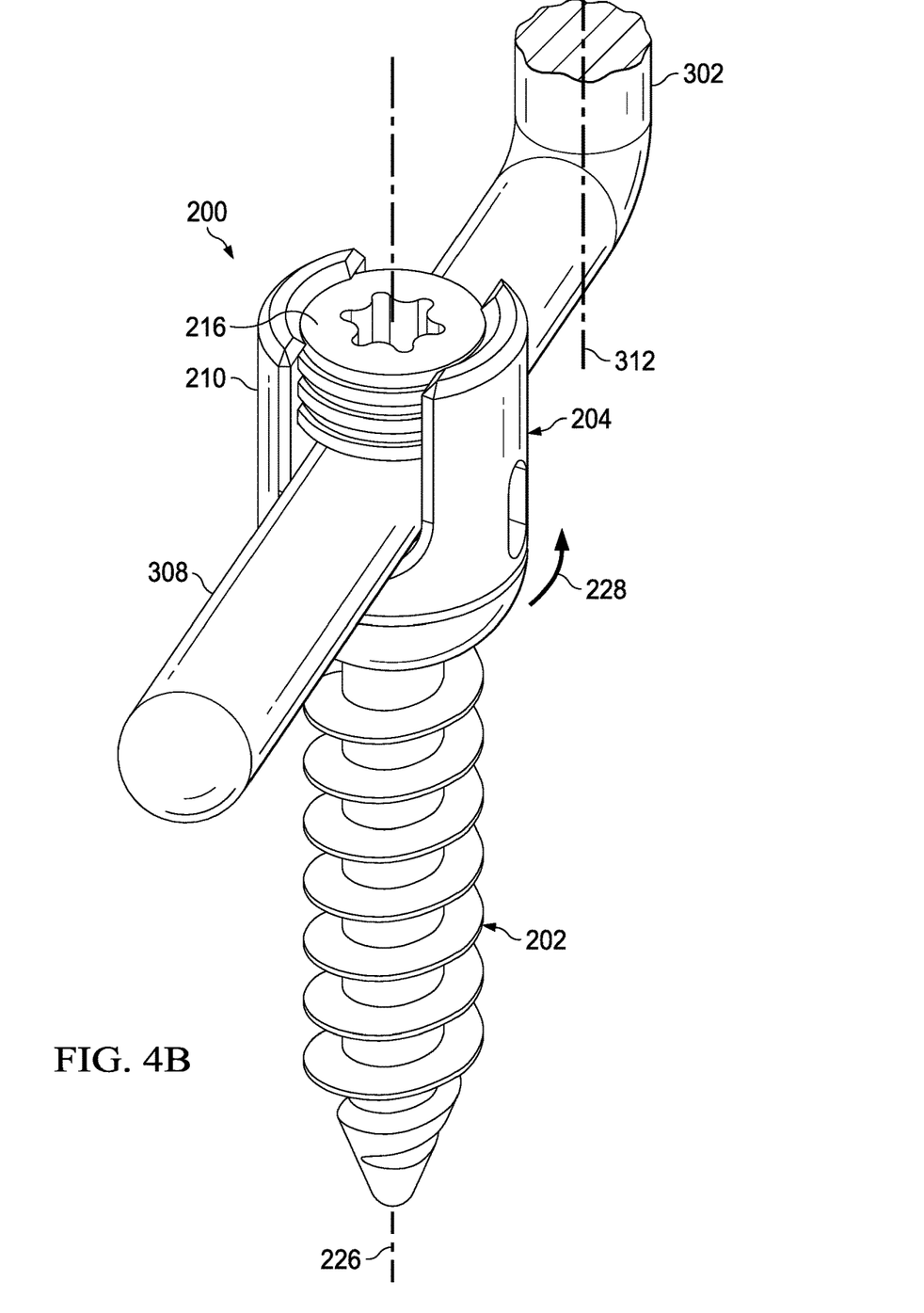
FIG. 4B is an isometric view of the preferred embodiment of FIG. 3A engaged with a tuliped pedicle screw.

Referring to FIGS. 4A and 4B, a method of using pedicle screw removal tool 300 to remove a tuliped pedicle screw will be further described.

Figure 4C:
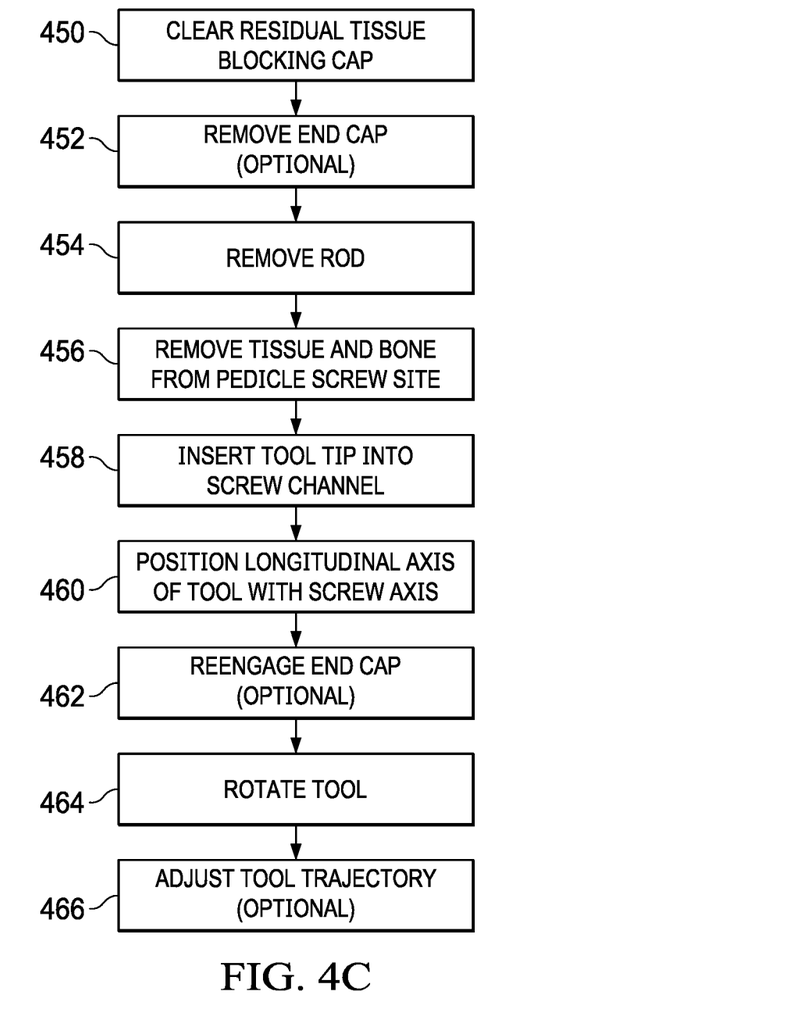
FIG. 4C is a flowchart of a preferred method of using the tool.

At step 450, residual tissue is cleared from the end cap from the pedicle screw. At step 452, end cap 216 is removed using the appropriate spanner, if possible. In cases of advanced bone growth, the cap may remain in place in the screw. However, preferably the cap is at least loosed sufficiently to dislodge and remove the stability rod. At step 454, stability rod 222 is removed. At step 456, remaining tissue surrounding body 204 of pedicle screw 200 is then removed. At step 458, tip 308 is inserted into channel 206 such that prong 314 is adjacent blades 208 and 210. At step 460, longitudinal axis 312 of pedicle screw removal tool 300 is positioned generally coplanar and parallel with longitudinal axis 226 of threaded section 202. Longitudinal axis 312 of pedicle screw removal tool 300 is generally positioned offset from longitudinal axis 226 of threaded section 202 such that the axes are not axially aligned. At step 462, end cap 216 is reengaged with body 204 to secure tip 308 to pedicle screw 200. Optionally, end cap 216 remains disengaged from body 204. In the event that end cap 216 is compromised and cannot be removed, tip 308 is inserted into channel 206 from the side and underneath end cap 216. At step 464, pedicle screw removal tool 300 is rotated in direction 228 around pedicle screw 200, generally counter-clockwise, to unscrew pedicle screw 200 from the bone. Rotation of pedicle screw removal tool 300 can be accomplished by use of handle 306 or, if necessary, a torque producing tool such as a ratchet attached to head 310. Motorized torque producing tools may also be employed. At step 466, the trajectory of the tool may optionally be adjusted to a different angle by loosening the end cap, realigning the axis of the tool with respect to the screw and retightening the end cap.

Use of pedicle screw removal tool 300 eliminates the need to locate a matching removal tool for the pedicle screw regardless of whether or not the socket has been compromised. This procedure improves the speed and accuracy of pedicle screw removal as time is not wasted locating the proper sized tool, or fabricating custom tools. Further, safety is improved by reducing time required attending to unnecessary tissue damage and contamination.

Figure 5:
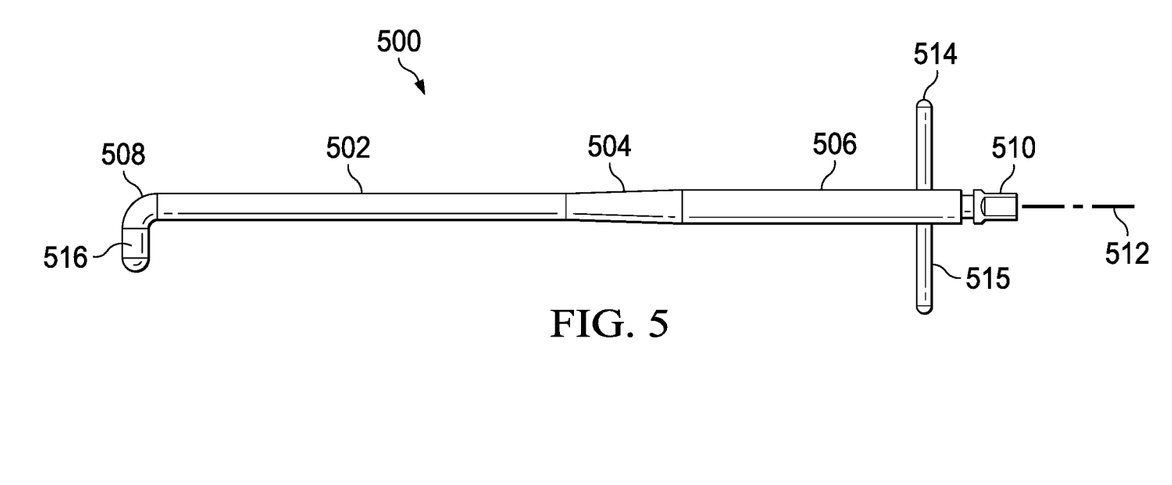
FIG. 5 is a side view of an alternate preferred embodiment.

Referring to FIG. 5, an alternate embodiment will be described. Pedicle screw removal tool 500 is a generally cylindrical shaft comprising lower section 502 integrally formed with and connected to neck 504. Neck 504 is integrally formed with and connected to handle 106. Neck 504 radially expands from lower section 502 to handle 506. Tip 508 is integrally formed with and connected to lower section 502 opposite neck 504. Head 510 is integrally formed with and connected to handle 506 opposite neck 504. Lower section 502 is axially aligned with neck 504. Neck 504 is axially aligned with handle 506. Handle 506 is axially aligned with head 510. Lower section 502, neck 504, handle 506, and head 510 all share central longitudinal axis 512. Handle 506 further includes opposing members 514 and 515. Tip 508 is generally "L" shaped formed by prong 516. Prong 516 extends from tip 508 generally perpendicular to lower section 502. In a preferred embodiment, pedicle screw removal tool 500 is constructed of surgical grade steel.

The overall length of pedicle screw removal tool 500 can range from approximately eight to twelve inches depending on desired use. Prong 516 generally ranges from ⅛ to ½ inch in diameter. The length of prong 516 ranges from approximately ½ to one inch. Lower section 502 ranges in length from approximately three to five inches. Lower section 502 generally ranges from ⅛ to ½ inch in diameter. The length of neck 504 ranges from approximately one to two inches. Neck 504 is a generally frustoconical shape with an increasing diameter from a range of ⅛ to ½ inch in diameter at the connection of neck 504 to lower section 502 to a range of ½ inch to ¾ inch in diameter at the connection of neck 504 to handle 506. Handle 506 ranges in length from approximately three to four inches. Handle 506 generally ranges from ½ to ¾ inch in diameter. Members 514 and 515 are generally cylindrical (however, other cross-sections are envisioned), are axially aligned, and extend from handle 506 generally perpendicular to handle 506. Members 514 and 515 each range in length from approximately one and ½ to two inches. Members 514 and 515 generally range from ½ to ¾ inch in diameter. Head 510 ranges in length from approximately ½ to one inch. Head 510 has a generally square cross-section width a width that ranges from approximately ⅛ to ¾ of an inch. In alternate embodiments, head 510 may have other polygonal cross-sectional shapes suitable for attachment of a torque producing tool.

In use, in addition to the previous methods discussed, members 514 and 515 may be used to assist in the rotation of pedicle screw removal tool 500 in order to remove tuliped pedicle screws.

Figure 6:
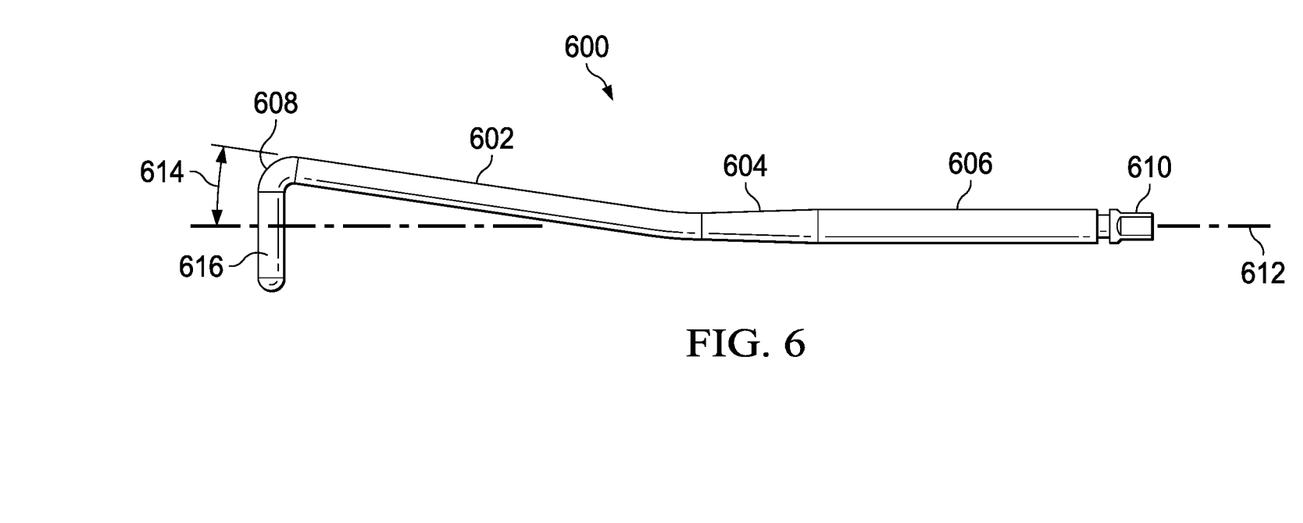
FIG. 6 is a side view of an alternate preferred embodiment.

Referring to FIG. 6, an alternate embodiment will be described. Pedicle screw removal tool 600 is a generally tapered cylindrical shaft comprising an angled lower section 602 integrally formed with neck 604. Neck 604 is integrally formed with handle 606. Tip 608 is integrally formed with lower section 602 opposite neck 604. Head 610 is integrally formed with handle 606 opposite neck 604. Lower section 302 extends at angle 614 from neck 604. Neck 604 is axially aligned with handle 606. Handle 606 is axially aligned with head 610. Neck 604, handle 606, and head 610 all share central longitudinal axis 612. Tip 608 is generally "L" shaped formed by prong 616. Prong 616 extends from tip 608 generally perpendicular to longitudinal axis 612. Longitudinal axis 612 intersects prong 616. In a preferred embodiment, pedicle screw removal tool 600 is constructed of surgical grade stainless steel.

The overall length of pedicle screw removal tool 600 can range from approximately eight to twelve inches depending on desired use. Prong 616 generally ranges from ⅛ to ½ inch in diameter. The length of prong 616 ranges from approximately ½ to one inch. Lower section 602 ranges in length from approximately three to five inches. Lower section 602 generally ranges from ⅛ to ½ inch in diameter. Angle 614 ranges from approximately 15° to 45°. The length of neck 604 ranges from approximately one to two inches. Neck 604 is a generally frustoconical shape with an increasing diameter from a range of ⅛ to ½ inch in diameter at the connection of neck 604 to lower section 602 to a range of ½ inch to ¾ inch in diameter at the connection of neck 604 to handle 606. Handle 606 ranges in length from approximately three to four inches. Handle 606 generally ranges from ½ to ¾ inch in diameter. Head 610 ranges in length from approximately ½ to one inch. Head 610 has a generally square cross-section width a width that ranges from approximately ⅛ to ¾ of an inch. In alternate embodiments, head 610 may have other polygonal cross-sectional shapes suitable for attachment of a torque producing tool.

Figure 7:
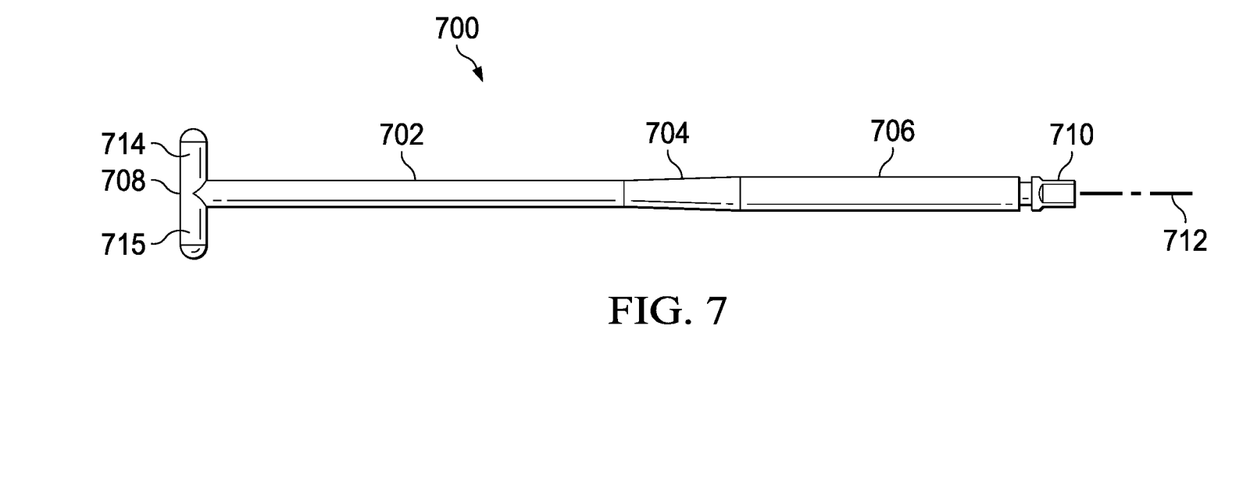
FIG. 7 is a side view of an alternate preferred embodiment.

Referring to FIG. 7, an alternate embodiment will be described. Pedicle screw removal tool 700 is a generally tapered cylindrical shaft comprising lower section 702 integrally formed with and connected to neck 704. Neck 704 is integrally formed with and connected to handle 706. Tip 708 is integrally formed with and connected to lower section 702 opposite neck 704. Head 710 is integrally formed with and connected to handle 706 opposite neck 704. Lower section 702 is axially aligned with neck 704. Neck 704 is axially aligned with handle 706. Handle 706 is axially aligned with head 710. Lower section 702, neck 704, handle 706, and head 710 all share longitudinal axis 712. Tip 708 is generally "T" shaped formed by prongs 714 and 715. Prongs 714 and 715 are axially aligned and extend from tip 708 generally perpendicular to lower section 702. The twin prongs of pedicle screw removal tool 700 are important in cases where access to the screw channel is obstructed from one side or the other. In these cases, either prong may be used in the channel to remove the screw. In a preferred embodiment, pedicle screw removal tool 700 is constructed of surgical grade stainless steel.

The overall length of pedicle screw removal tool 700 can range from approximately eight to twelve inches depending on intended use. Prong 714 and 715 generally range from ⅛ to ½ inch in diameter. The length of each prong 714 and 715 ranges from approximately ¼ to ½ inch. Lower section 702 ranges in length from approximately three to five inches. Lower section 702 generally ranges from ⅛ to ½ inch in diameter. The length of neck 704 ranges from approximately one to two inches. Neck 704 generally expands from a range of ⅛ to ½ inch in diameter at the connection of neck 704 to lower section 702 to a range of ½ inch to ¾ inch in diameter at the connection of neck 704 to handle 706. Handle 706 ranges in length from approximately three to four inches. Handle 706 generally ranges from ½ to ¾ inch in diameter. Head 710 ranges in length from approximately ½ to 1 inch. Head 710 has a generally square cross-section width a width that ranges from approximately ½ to ¾ of an inch. In alternate embodiments, head 710 may have other polygonal cross-sectional shapes suitable for attachment of a torque producing tool.

Figure 8:
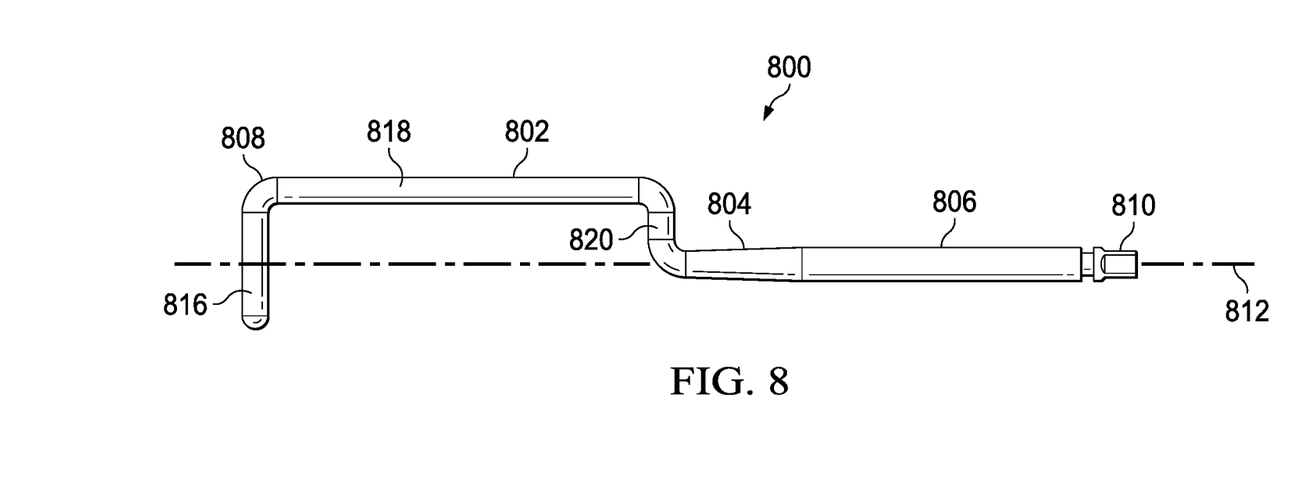
FIG. 8 is a side view of an alternate preferred embodiment.

Referring to FIG. 8, an alternate embodiment will be described. Pedicle screw removal tool 800 is a generally tapered cylindrical shaft comprising a offset lower section 802 integrally formed with neck 804. Neck 804 is integrally formed with handle 806. Tip 808 is integrally formed with lower section 802 opposite neck 804. Head 810 is integrally formed with handle 806 opposite neck 804. Neck 804 is axially aligned with handle 806. Handle 806 is axially aligned with head 810. Neck 804, handle 806, and head 810 all share central longitudinal axis 812. Lower section 802 comprises segments 818 and 820. Segment 818 is generally parallel with longitudinal axis 812 and connects segment 820 to tip 808. Segment 820 extends generally perpendicular to longitudinal axis 812 from neck 804. Prong 816 extends from segment 818 generally perpendicular to longitudinal axis 812. Longitudinal axis 812 intersects prong 816. In a preferred embodiment, pedicle screw removal tool 800 is constructed of surgical grade stainless steel.

The overall length of pedicle screw removal tool 800 can range from approximately eight to twelve inches depending on desired use. The length of prong 816 ranges from approximately ½ to 1 inch. Prong 816 generally ranges from ⅛ to ½ inch in diameter. Lower section 802 ranges in length from approximately three to five inches. Lower section 802 generally ranges from ⅛ to ½ inch in diameter. Segment 820 ranges in length from approximately ½ to 1 inch. Segment 820 generally ranges from ⅛ to ½ inch in diameter. The length of neck 804 ranges from approximately one to two inches. Neck 804 is a generally frustoconical shape with an increasing diameter from a range of ⅛ to ½ inch in diameter at the connection of neck 804 to lower section 802 to a range of ½ inch to ¾ inch in diameter at the connection of neck 804 to handle 806. Handle 806 ranges in length from approximately three to four inches. Handle 806 generally ranges from ½ to ¾ inch in diameter. Head 810 ranges in length from approximately ½ to 1 inch. Head 810 has a generally square cross-section width a width that ranges from approximately ⅛ to ¾ of an inch. In alternate embodiments, head 810 may have other polygonal cross-sectional shapes suitable for attachment of a torque producing tool.

Figure 9:
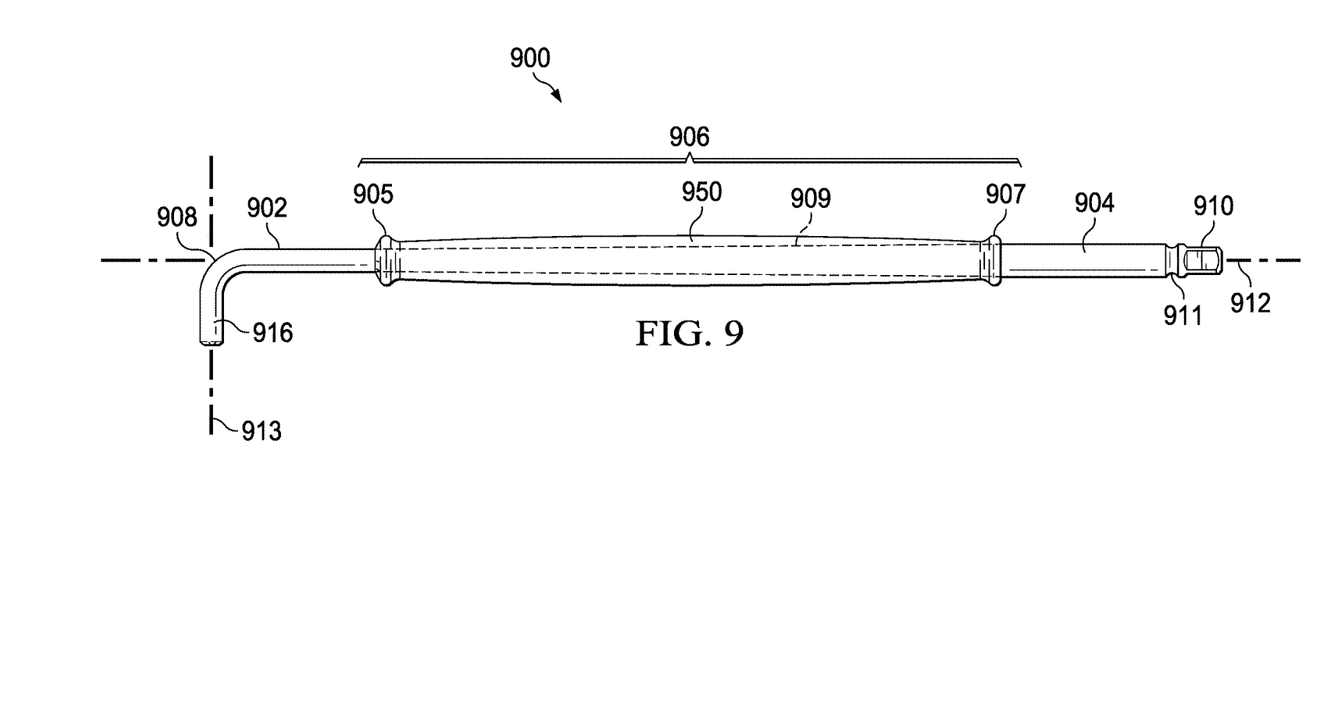
FIG. 9 is a side view of an alternate preferred embodiment.

Referring to FIG. 9, an alternate embodiment will be described. Pedicle screw removal tool 900 is generally a cylindrical shaft comprising lower section 902 integrally formed with and connected to center section 909 and neck 904. Tip 908 is integrally formed with and connected to lower section 902 opposite neck 904. Lower section 902 is axially aligned with neck 904. Neck 904 is generally of a larger diameter than lower section 902. The diameter of the tool is reduced gradually within the handle along center section 909, which is frustoconical in shape. Neck 904 is axially aligned with handle 906. Handle 906 is axially aligned with head 910. In a preferred embodiment, head 910 is a ¼ inch square cross section adapted to fit a ratchet drive. Annular indention 911 is positioned adjacent and distal to head 910. In a preferred embodiment, annular indention 911 and head 910 are adapted to fit an AO connect handle or a T-handle as known in the art.

In a preferred embodiment, handle 906 is comprised of angular end stop 905 connected to convex center section 950 and angular end stop 907. Handle 906, in a preferred embodiment, is integrally formed of a nitrile rubber, a polyethylene plastic, or a Teflon® material, inductively welded to the tool to prevent movement of the handle with respect to center section 909. Other medical grade pliable and flexible rubber or pliable plastic or polymeric materials can be used. Handle 906 is generally cylindrical and surrounds the tool having a common axis in a common central axis with the tool. Lower section 902, neck 904, handle 906 and head 910 all share longitudinal axis 912. Tip 908 is generally L-shaped including prong 916. Prong 916 extends from lower section 902 generally perpendicular to longitudinal axis 912. Longitudinal axis 912 intersects the axis of prong 916 intersects axis 913 of prong 916. In a preferred embodiment, pedicle screw removal tool 900 is constructed of rigid, unbendable surgical grade stainless steel, with dimensions similar to those previously described.

Pedicle screw removal tools 600, 700, 800 and 900 can each be used to remove any size tuliped pedicle screw.

In use, end cap 216 is removed. Rod 222 is removed. Tissue surrounding body 204 of the pedicle screw is removed. When using tool 600, tip 608 is inserted into channel 206 such that prong 616 is adjacent blades 208 and 210. When using tool 700, tip 708 is inserted into channel 206 such that prongs 714 and 715 are adjacent blades 208 and 210. When using pedicle screw removal tool 800, tip 808 is inserted into channel 206 such that prong 816 is adjacent blades 208 and 210. In the case of tools 600, 700 and 800, longitudinal axis 612, 712, or 812 is positioned generally coaxial with longitudinal axis 226 of threaded section 202. The pedicle screw removal tool is rotated, generally counter-clockwise, to dislodge pedicle screw 200 from its attachment to the bone. Rotation of the pedicle screw removal tool can be accomplished by hand using the handle or, if necessary, a torque producing tool such as a wrench or ratchet can be attached to the head.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

The invention claimed is:

1. A tool and a tuliped pedicle screw combination, the tuliped pedicle screw having a first longitudinal axis and a channel, the channel defined by a first blade and a second blade, the tool comprising:
   an unbendable cylindrical shaft, having a second longitudinal axis;
   a tip, fixed to the unbendable cylindrical shaft, having a first prong extending perpendicularly from the unbendable cylindrical shaft and fixed in the channel adjacent the first blade and the second blade with the second longitudinal axis coplanar with the first longitudinal axis;
   a tool connector head, fixed to the unbendable cylindrical shaft, opposite the tip; and,
   wherein rotation of the tool removes the tuliped pedicle screw.

2. The tool of claim 1 wherein:
   the tool connector head comprises a square cross section, the square cross section having a dimension of between ⅛ inch to ½ inch across; and,
   the first prong has a diameter of between ¼ inch and ½ inch.

3. The tool of claim 1 wherein the unbendable cylindrical shaft further includes an offset angle section, between the tip and the tool connector head, for centering the first prong with respect to the second longitudinal axis.

4. The tool of claim 1 further comprising a torque imposing tool affixed to the tool connector head.

5. A pedicle screw removal tool and a tuliped pedicle screw, the tuliped pedicle screw having a first longitudinal axis and a transverse channel, the pedicle screw removal tool comprising:
   a rigid shaft having a second longitudinal axis;
   a tool connection head, coaxial with the second longitudinal axis and connected to the rigid shaft;
   a first engagement means engaged with the transverse channel, extending from the rigid shaft, perpendicularly to the second longitudinal axis;
   wherein the first longitudinal axis is coplanar with the second longitudinal axis; and,
   wherein rotation of the pedicle screw removal tool removes the tuliped pedicle screw.

6. The pedicle screw removal tool of claim 5 wherein the rigid shaft further comprises:
   an angled section extending at an acute angle with respect to the second longitudinal axis; and,
   the first engagement means positioned to intersect the second longitudinal axis.

7. The pedicle screw removal tool of claim 5 further comprising:
   a first torque imposing member extending perpendicularly from the rigid shaft;
   a second torque imposing member extending perpendicularly from the rigid shaft; and,
   wherein the first torque imposing member and the second torque imposing member are coaxial.

8. A tool for the removal of a tuliped pedicle screw, the tuliped pedicle screw having a first longitudinal axis and a channel, the channel defined by a first blade and a second blade, the tool comprising:

an unbendable cylindrical shaft, having a second longitudinal axis;
a tip, fixed to the unbendable cylindrical shaft, having a first prong extending perpendicularly from the unbendable cylindrical shaft for placement in the channel adjacent the first blade and the second blade with the second longitudinal axis configured to be coplanar with the first longitudinal axis; and,
a tool connector head, fixed to the unbendable cylindrical shaft, opposite the tip;
wherein the tip includes a second prong, extending perpendicular from the unbendable cylindrical shaft; and,
wherein the second prong is axially aligned with the first prong.

9. A pedicle screw removal tool for removing a tuliped pedicle screw, the tuliped pedicle screw having a first longitudinal axis and a transverse channel, the pedicle screw removal tool comprising:
a rigid shaft having a second longitudinal axis;
a tool connection head, coaxial with the second longitudinal axis and connected to the rigid shaft;
a first engagement means for engagement with the transverse channel, extending from the rigid shaft, perpendicularly to the second longitudinal axis;
wherein the first longitudinal axis is configured to be coplanar with the second longitudinal axis;
a second engagement means for engagement with the transverse channel, extending perpendicularly from the rigid shaft and coaxial with the first engagement means; and,
wherein the second longitudinal axis is configured to be axially aligned with the first longitudinal axis.

10. A pedicle screw removal tool for removing a tuliped pedicle screw, the tuliped pedicle screw having a first longitudinal axis and a transverse channel, the pedicle screw removal tool comprising:
a rigid shaft having a second longitudinal axis;
a tool connection head, coaxial with the second longitudinal axis; and connected to the rigid shaft;
a first engagement means for engagement with the transverse channel, extending from the rigid shaft, generally perpendicularly to the second longitudinal axis;
wherein the first longitudinal axis is configured to be coplanar with the second longitudinal axis; and,
a flexible polymeric grip surrounding the rigid shaft.

11. The pedicle screw removal tool of claim 10 wherein the flexible polymeric grip is immovably bonded to an exterior surface of the rigid shaft.

12. A method of removing a tuliped pedicle screw, the tuliped pedicle screw having a first longitudinal axis and a channel, the channel defined by a first blade and a second blade, the method comprising:
providing a tool having an off axis angular tip rigidly connected to an unbendable cylindrical shaft, the unbendable cylindrical shaft having a second longitudinal axis;
engaging the off axis angular tip with the channel;
positioning the first longitudinal axis and the second longitudinal axis in a coplanar relationship; and,
rotating the unbendable cylindrical shaft axially to apply a rotational force to the first blade and the second blade to remove the tuliped pedicle screw.

13. The method of claim 12 further comprising:
securing the off axis angular tip to the tuliped pedicle screw with an end cap.

14. The method of claim 12 wherein the unbendable cylindrical shaft further comprises:
an angular section for positioning the off axis angular tip into coaxial alignment with the first longitudinal axis; and,
wherein the method further comprises:
positioning the first longitudinal axis and the second longitudinal axis in a collinear relationship.

15. The method of claim 14 further comprising:
rotating the unbendable cylindrical shaft about one of the first longitudinal axis and the second longitudinal axis.

16. The method of claim 12, wherein the off axis angular tip comprises a first prong extending perpendicularly from the unbendable cylindrical shaft and a second prong extending perpendicularly from the unbendable cylindrical shaft and wherein the method further comprises;
engaging the channel with one of the first prong and the second prong; and,
repositioning the first longitudinal axis and the second longitudinal axis in a coaxial relationship.

17. The method of claim 16 further comprising:
rotating the unbendable cylindrical shaft about one of the first longitudinal axis and the second longitudinal axis.

18. The method of claim 12 wherein the unbendable cylindrical shaft comprises a set of rigid opposing torque imposing members radially extending from the unbendable cylindrical shaft; and, wherein the method further comprises:
rotating the unbendable cylindrical shaft by applying the rotational force to the set of rigid opposing torque imposing members.

19. The method of claim 12 wherein the unbendable cylindrical shaft comprises a tool connection head axially connected to the unbendable cylindrical shaft;
connecting a torque imposing tool to the tool connection head; and, wherein the method further comprises:
rotating the unbendable cylindrical shaft by applying the rotational force to the torque imposing tool.

20. The method of claim 19 wherein the torque imposing tool comprises a ratchet.

21. The method of claim 12 further comprising the step of:
adjusting a trajectory of the tool to disalign the first longitudinal axis and the second longitudinal axis.

* * * * *